United States Patent [19]

Hobbs et al.

[11] Patent Number: 5,234,567
[45] Date of Patent: Aug. 10, 1993

[54] GAS SENSOR

[75] Inventors: Bryan S. Hobbs, Chertsey; Yat S. Chan, London, both of United Kingdom

[73] Assignee: City Technology Limited, Portsmouth, England

[21] Appl. No.: 824,510

[22] Filed: Jan. 23, 1992

[30] Foreign Application Priority Data

Jan. 25, 1991 [GB] United Kingdom ............... 9101643

[51] Int. Cl.$^5$ ........................................... G01N 27/26
[52] U.S. Cl. .................................. 204/415; 204/422; 204/424; 204/431
[58] Field of Search ............... 204/412, 415, 153.15, 204/153.17, 422, 424

[56] References Cited

U.S. PATENT DOCUMENTS

| | | | |
|---|---|---|---|
| 3,764,269 | 10/1973 | Oldham | 23/254 E |
| 3,821,090 | 6/1974 | Topol et al. | 204/415 |
| 4,474,648 | 10/1984 | Tantrum et al. | 204/415 |
| 4,568,445 | 2/1986 | Cates et al. | 204/412 |
| 4,842,697 | 6/1989 | Driscoll et al. | 204/415 |
| 5,076,904 | 12/1991 | Kiesele et al. | 204/415 |

FOREIGN PATENT DOCUMENTS

| | | |
|---|---|---|
| 0395927 | 11/1990 | European Pat. Off. . |
| 2624266 | 12/1977 | Fed. Rep. of Germany . |
| 2225859 | 6/1990 | United Kingdom . |

OTHER PUBLICATIONS

Miller et al, "A Versatile Electrochemical Monitor For Air-Quality Measurements", J. Air Pollution Control Assn., Jul. 1971, vol. 21, No. 7, pp. 414-417.

*Primary Examiner*—John Niebling
*Assistant Examiner*—Bruce F. Bell
*Attorney, Agent, or Firm*—Lee, Mann, Smith, McWilliams, Sweeney & Ohlson

[57] ABSTRACT

An electrochemical gas sensor for sensing an alkaline gas such as ammonia. The sensor comprises at least sensing and counter electrodes provided in a cell containing an aqueous electrolyte, the cell further including a diffusion barrier to restrict the access of gas to the cell, and a chemical species with which the gas reacts in use to form a product which is more electrochemically active than the gas. The chemical species is one of iodine, Nesslers reagent and a solution of manganous and silver nitrates.

8 Claims, 4 Drawing Sheets

GAS SENSOR

FIELD OF THE INVENTION

The invention relates to electrochemical gas sensors.

DESCRIPTION OF THE PRIOR ART

Amperometric, electrochemical sensors have been widely adopted to meet a growing demand for suitable measuring devices in safety and process control applications. These sensors operate on fuel cell and battery principles utilising the direct electrochemical oxidation or reduction of the gas to be measured at a gas diffusion electrode, in combination with a gaseous diffusion barrier, to produce an electrical signal which is directly related to the concentration of gas being measured.

A paper entitled "A Versatile Electrochemical Monitor For Air-Quality Measurements" by Miller et al, Journal of the Air Pollution Control Association, Vol. 21, No. 7 (Jul. 1971), pages 414-417 describes an electrochemical instrument for measuring acid gases. However, this technique, which involves reacting a gas to be sensed with an aqueous mixture of iodate and iodide has never been considered suitable for sensing alkaline gases such as ammonia.

U.S. Application No. 3821090 (and also U.S. Application No. 3774269) describes a cell for measuring the acid gas $NO_2$. These work on similar principles to those described above in the Miller et al article and are not readily adaptable to the detection of alkaline gases.

In principle, ammonia gas could be detected by means of an amperometric gas sensor, using the direct anodic oxidation reaction:

$$2NH_3 = N_2 + 6H + 6e \quad (1)$$

In practice ammonia forms the ammonium ion ($NH_4^+$) in the aqueous solution comprising the sensor electrolyte:

$$NH_3 + H_2O = NH_4^+ + OH \quad (2)$$

This ion is particularly stable and does not readily undergo electrochemical reaction. In acid solutions $NH_4^+$ is the predominant species and no response can be obtained from sensors by direct oxidation, even when utilising very active electrocatalysts such as platinum, at extreme anodic overpotentials, at which the oxygen evolution reaction occurs to a significant extent and imposes an unacceptable background current. In electrolyte solutions of higher pH the equilibrium of equation (2) lies further to the left hand side and some direct anodic oxidation response can be achieved. However, even in strong alkali, the $N_3$ oxidation signals suffer undesirable effects such as slow response, hysteresis on removal of the test gas and signal decay and drift. Furthermore, since active electrode catalysts are required such as platinum, the sensors suffer from cross interferences from other gases, such as carbon monoxide, hydrogen, etc. which may co-exist with ammonia in the atmosphere being monitored. An example of a sensor which directly detects the oxidation of ammonia is described in EP-A-0395927 published on 14 Apr. 1990 (and thus not a prior publication). GB-A-2225859 describes a measuring cell for determining ammonia in which the electrolyte contains a soluble non-oxidizable reagent which reacts completely with ammonia to form an oxidizable product which is able to be converted by oxidation into a non-oxidizable, soluble and, chemically and electrochemically inert secondary product. The preferred reagent is an organic ammonium salt which reacts with ammonia to form an amine. Commercial products incorporating this idea have a significant size which makes them generally undesirable and have a poor low temperature performance.

SUMMARY OF THE INVENTION

In accordance with the present invention, an electrochemical gas sensor for sensing an alkaline gas comprises at least sensing and counter electrodes provided in a cell containing an aqueous electrolyte, the cell further including a diffusion barrier to restrict the access of gas to the cell, and a chemical species with which the gas reacts in use to form a product which is more electrochemically active than the gas, wherein the chemical species is one of:

a) iodine;
b) Nesslers reagent; and
c) a solution of manganous and silver nitrates.

The invention is particularly suitable for the detection of ammonia and the preferred chemical reagent is iodine. Ammonia dissolves readily in water to produce alkali in accordance with reaction (2) above and iodine reacts in the alkaline conditions formed producing iodide and iodate ions according to the equation:

$$6OH + 3I_2 = 5I + IO_3 + 3H_2O \quad (3)$$

The iodide ion (I) readily undergoes electrochemical oxidation at the sensing electrode to provide a current which is directly related to the ammonia concentration and regenerates iodine in part for further reaction:

$$2I = I_2 + 2e \quad (4)$$

The overall sensor reaction, providing a measure of the ammonia concentration is then the combination of equations (2), (3) and (4), namely:

$$12NH_3 + 6H_2O + I_2 = 2IO_3 + 12NH_4^+ + 10e \quad (5)$$

Any gas producing an alkaline reaction in water would produce a response in a sensor based on reaction (5) above. Alkaline gases include hydrazines and organic amines. However, for most applications ammonia is the only gas likely to be present producing an alkaline reaction. Since the iodide/iodine reaction (4) proceeds readily on moderately active catalysts, interferences from likely co-existing gases with ammonia such as carbon monoxide, hydrogen, etc. can be avoided. Acidic gases such as carbon dioxide, sulphur dioxide, etc. will not react with the iodine in solution and will not therefore produce a response from the sensor provided they do not themselves undergo direct electrochemical reaction at the electrode catalyst.

The sensor electrolyte solution should have low pH buffer capacity to provide optimum sensitivity to the dissolving ammonia gas; it should also contain an ionically conducting supporting electrolyte. To meet these requirements salts of strong acids and strong bases are dissolved in the solution containing iodine. Examples of suitable electrolytes are salts of the alkali and alkaline earth metals such as the chlorides of lithium, sodium, potassium, calcium etc. Salts such as lithium and calcium chlorides are hygroscopic and provide the additional benefit of controlling the sensor water balance, preventing the sensor from drying out.

Although some of the reacted iodine is regenerated by electrochemical oxidation of the iodide product (equation 4) there is a net consumption of iodine according to equation 5 of 1 mole per 12 moles of ammonia. The sensor life will therefore be determined by the volume of electrolyte and iodine concentration contained in the sensor. Iodine only has a limited solubility in water but measures can be taken to increase the iodine capacity of the sensor, without the need to carry a large volume of electrolyte. Free solid iodine contained within the electrolyte reservoir would ensure that the solution remains saturated with iodine; however, solid iodine has a measurable vapour pressure and slowly diffuses out of the sensor. In addition to lost iodine capacity, the volatile iodine can cause problems of corrosion to metal surfaces external to the cell.

In one approach, the iodine is bound chemically to another compound, such as starch, which releases iodine reversibly as free iodine in equilibrium with the complex. In this way sufficient iodine is available to satisfy the sensing electrode reactions for detecting ammonia, but at a sufficiently low concentration to reduce iodine loss by volatilisation to an extremely low level. The starch complex also allows a considerable iodine capacity to be obtained in a relatively small electrolyte volume. An alternative approach would be to implant a permeation device inside the sensor, containing an iodine source and which is designed to have suitably low iodine diffusion rate so as to provide a controlled release of iodine into the electrolyte to maintain the concentration at the appropriate level. The iodine source may be for example, solid iodine, aqueous or non-aqueous iodine solutions or any compound which may release elemental iodine which can then diffuse at a controlled rate from the capsule, into the body of the sensor and thence into its electrolyte.

In one alternative, but less preferred, arrangement the electrolyte contains Nesslers Reagent. This comprises a solution of mercuric iodide, dissolved in excess potassium iodide solution in which the complex mercuric-iodide ions $HgI_3$ and $HgI_4$ are formed. These complexes do not precipitate mercuric oxide on adding alkali but do give a yellow-brown coloration with $NH_3$ forming the amino component $Hg_2OINH_2$, the iodide of "Millons Base" ($Hg_2O(OH)NH_2$). This compound can then undergo anodic oxidation of the amino group to produce the signal of the sensor. This reagent is not a preferred material since the mercury salt would impose problems with disposal of the sensors at end of their life.

In a further arrangement the electrolyte can contain a solution of manganous and silver nitrates which reacts with hydroxide liberated by the dissolution of ammonia gas according to the equation:

$$Mn^{+++} + 2Ag + 4OH = MnO_2 + 2Ag + 2H_2O. \quad (6)$$

Following this reaction, either the $MnO_2$ can be cathodically reduced or the Ag anodically oxidised to produce the sensor signal related to the $NH_3$ concentration.

The diffusion barrier can be of any conventional type including a gas phase diffusion barrier, a Knudsen barrier, a solid barrier or a combination of two or more of these.

Although the sensor can have just sensing and counter electrodes, in general a third, reference electrode is provided to keep the sensing electrode at the correct, working potential.

It has been found that sensors according to the invention are of small size and have good low temperature performance.

BRIEF DESCRIPTION OF THE DRAWINGS

Some examples of sensors in accordance with the invention and a comparative example will now be described with reference to the accompanying drawings, in which.

DETAILED DESCRIPTION OF THE EMBODIMENTS

Figure 1A:
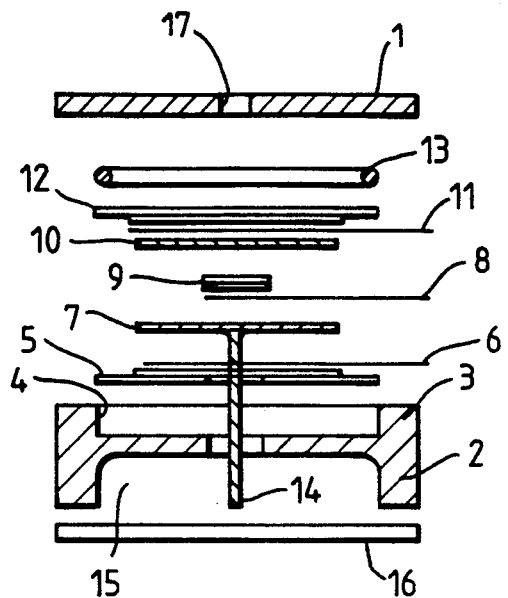
FIG. 1A is an exploded view of an example of a sensor according to the invention.
Figure 1B:
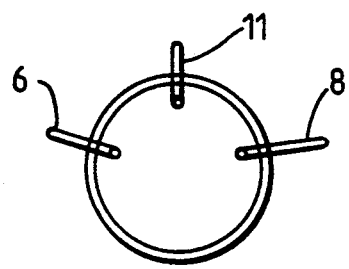
FIG. 1B illustrates the connections to the electrodes in the FIG. 1A example.
Figure 1C:
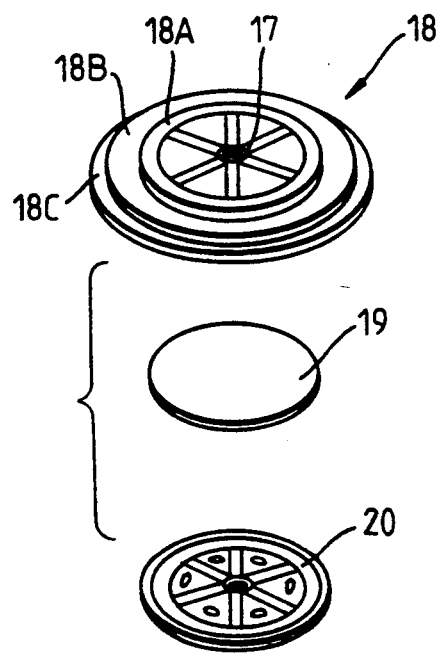
FIG. 1C is an exploded view of the top plate of FIG. 1A.

The sensor shown in FIGS. 1A–1C is generally of conventional form and will not be described in detail. Briefly, the sensor comprises a composite top plate 1 shown in more detail in FIG. 1C which is mounted in use to a base plate 2 having an outwardly facing, annular flange 3 defining an electrode well 4. Within the electrode well 4 are provided a counter electrode 5 comprising PTFE tape and a catalyst layer connected to a current collector 6. The counter electrode 5 is provided in a sandwich with a separator 7, a further current collector 8, a reference electrode 9 (comprising PTFE layer and catalyst), a separator 10, a current collector 11, and a sensing electrode 12 (again of PTFE and catalyst). Finally, an O-ring seal 13 is provided between the sensing electrode and the top plate 1. A wick 14 extends from the separator 7 through apertures in the counter electrode 5 and base plate 2 into an electrolyte reservoir 15 containing the electrolyte. The reservoir 15 is sealed by an end plate/seal 16.

The arrangement of the current collectors 6, 8, and 11 is shown in more detail in FIG. 1B.

A gas phase diffusion barrier is provided in the top plate 1 in the form of a capilliary 17. The construction of the top plate 1 is shown in more detail in FIG. 1C and comprises a capilliary plate 18 containing the capilliary 17, the plate having three sections 18A, 18B, and 18C of progressively increasing diameter. A Mupor tape filter 19 is fitted into the section 18B of the capilliary plate 18 while a capilliary plate mask 20 containing six equiangularly spaced, drilled holes of 1.1 mm diameter is snap fitted into the section 18C.

Three sensors were constructed to this established commercial design, (described also in GB Patent 2,094,005), incorporating a capillary diffusion barrier of six 1.1 mm diameter holes, a bonded, gas diffusion sensing electrode comprising a carbon based electrocatalyst, a silver/silver chloride reference electrode and a silver/silver iodate counter electrode. The sensors were primed with different electrolytes (described below)

and operated in an electrical control circuit according to Blazhenov et al (GB Patent 1,101,101, (1968)) with a +900 mV bias potential on the sensing electrode relative to the reference electrode.

Sensor 1. Primed with electrolyte consisting of 9M LiCl, 3.1M NaCl.

Sensor 2. Primed with electrolyte consisting of 9M Licl, 2.8M NaCl, saturated with $I_2$.

Sensor 3. Primed with electrolyte consisting of 7.7M LiCl, 2.8M NaCl, 1% starch, saturated with $I_2$.

Each sensor was allowed to settle for a week on the electrical control circuit, and the steady baseline (zero-gas response) noted. Responses to ammonia were then measured by exposing the sensors to a 41.3 ppm $NH_3$ (sensors 1 and 2) and 48.9 ppm $NH_3$ (sensor 3) in air test gas at a flow rate of 200 ml min$^{-1}$. Responses to the gases CO,$H_2$, $SO_2$ and $CO_2$ were similarly measured after the $NH_3$ exposure. Results of these tests are given in Table 1 below.

All 3 sensors had very low cross interferences to CO, $H_2$ and $CO_2$. Sulphur dioxide gave a significant response due to direct electrochemical oxidation in sensor 1 (about 200% $NH_3$ equivalent), but this was somewhat reduced with the $I_2$ systems at about 100%.

We claim:

1. An electrochemical gas sensor for sensing an alkaline gas, the sensor comprising at least sensing and counter electrodes provided in a cell containing an aqueous electrolyte, the cell further including a diffusion barrier to restrict the access of gas to the cell, and a chemical species with which the gas reacts ensue to form a product which is more electrochemically active than the gas, wherein said chemical species is one of:

a) iodine;

b) Nesslers reagent; and c) a solution of manganous and silver nitrates.

2. A sensor according to claim 1 for detecting ammonia, wherein said chemical species is iodine.

TABLE 1.

Characteristics of Ammonia Sensors.

| SENSOR | TEST GAS | BASELINE (ppm $NH_3$ equiv) | $NH_3$ RESPONSE (nA ppm$^{-1}$) | Cross Sensitivity (%) |
|---|---|---|---|---|
| 1. LiCl/NaCl | 41.3 ppm $NH_3$/air | 7.6 | 63 | |
| | 191 ppm CO/air | | | −0.2 |
| | 5% $CO_2$/air | | | zero |
| | 183 ppm $H_2$/air | | | zero. |
| | 194 ppm $SO_2$/$N_2$ | | | 196 |
| 2. LiCl/NaCl/$I_2$ | 41.3 ppm $NH_3$/air | 2.6 | 90 | |
| | 191 ppm CO/air | | | 0.1 |
| | 5% $CO_2$/air | | | zero |
| | 207 ppm $H_2$/air | | | −0.1 |
| | 194 ppm $SO_2$/air | | | 105 |
| 3. LiCl/NaCl/ $I_2$/starch | 48.9 ppm $NH_3$/air | 5.5 | 90 | |
| | 195 ppm CO/air | | | Zero |
| | 5% $CO_2$/air | | | zero |
| | 188 ppm $H_2$/air | | | Zero |
| | 194 ppm $SO_2$/air | | | 105 |

Figure 2:
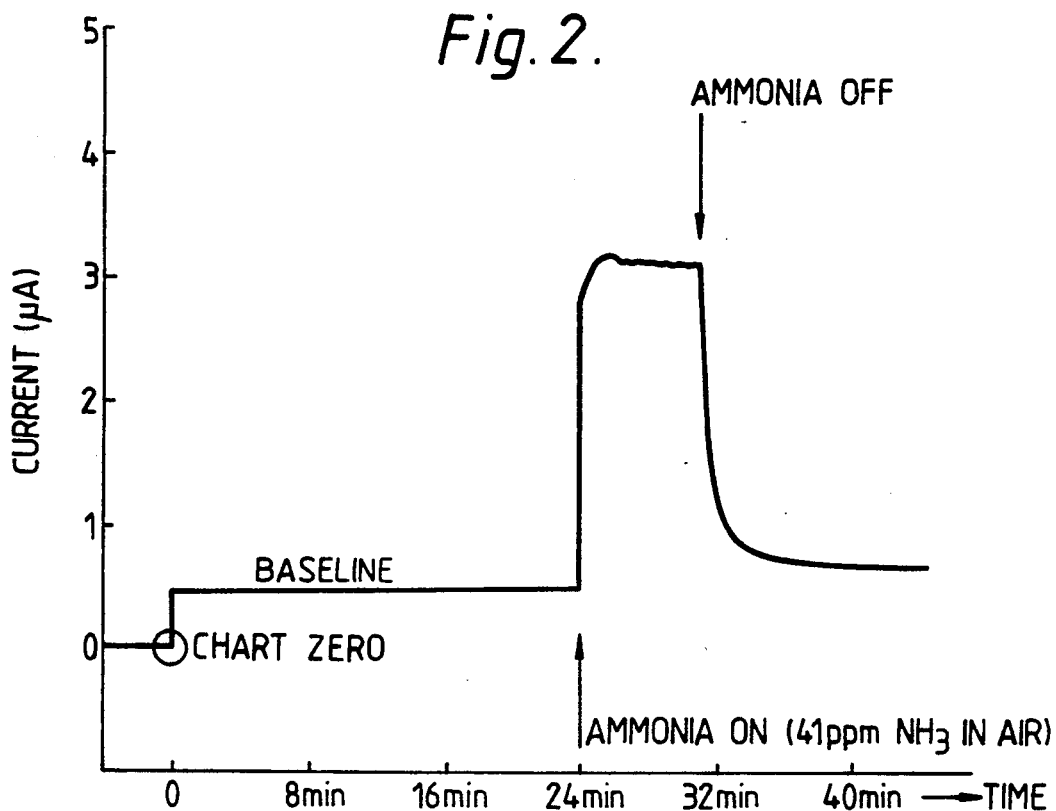
FIG. 2 illustrates the response of a conventional sensor after one week.
Figure 3:
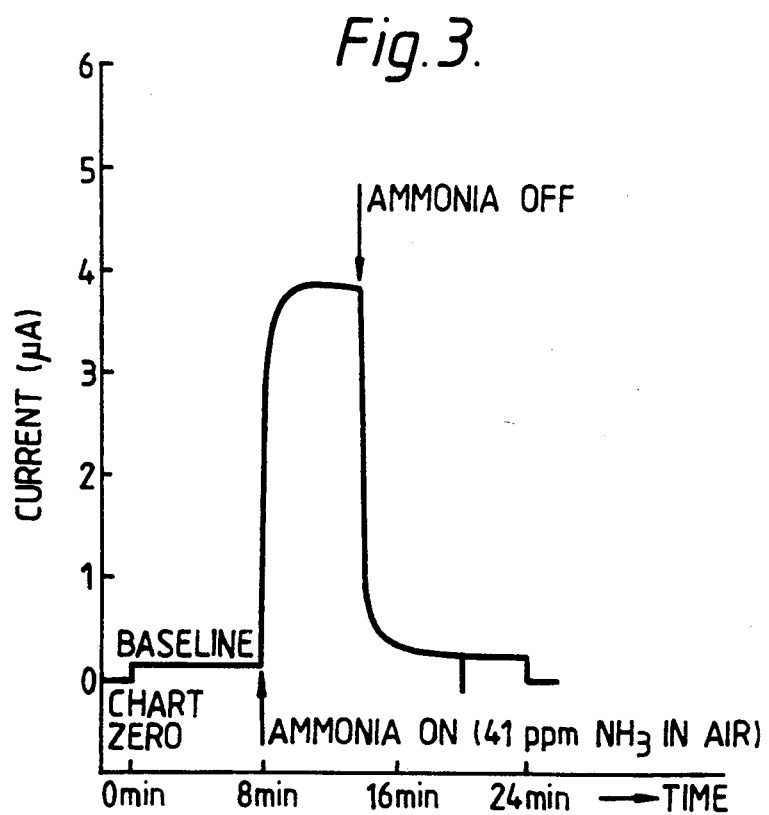
FIGS. 3 and 4 illustrate the response of two sensors according to the invention after one week.
Figure 4:
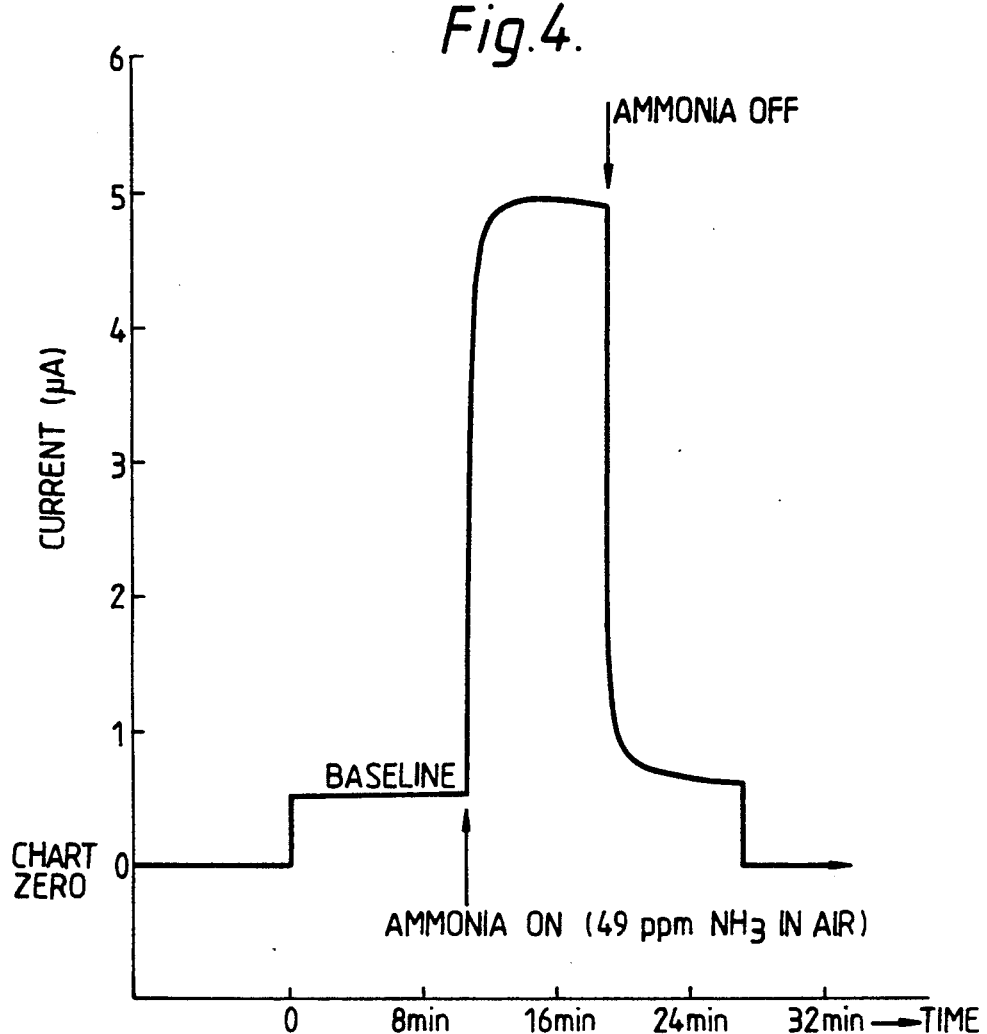
Figure 5:
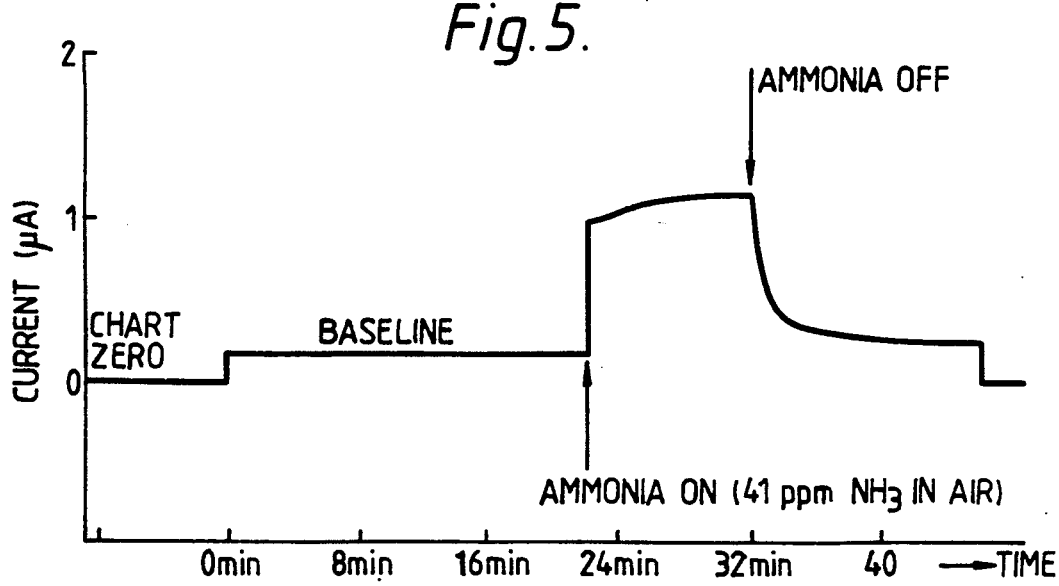
FIG. 5 illustrates the response of the conventional sensor after two weeks; and, FIG. 6 illustrates the sensitivity of a sensor according to the invention over a period of 11 weeks as well as that of a conventional sensor over 2 weeks.
Figure 6:
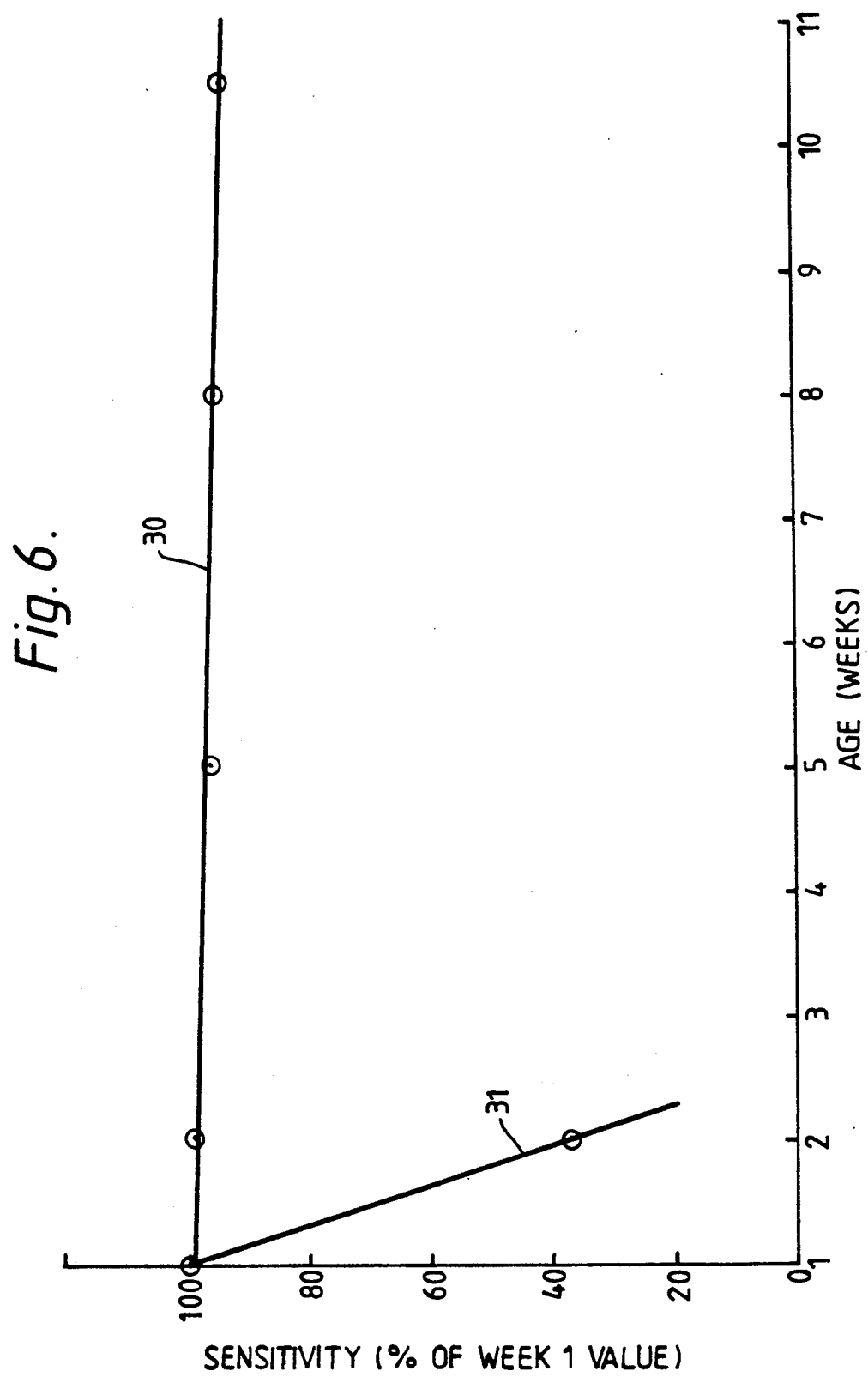

The (conventional) iodine-free electrolyte (sensor 1) produced a rather unstable response initially (FIG. 2) which suffered more hysteresis on removal of the test gas than either of the other two sensors (FIGS. 3 and 4). Furthermore, within 2 weeks the response of sensor 1 to $NH_3$ had reduced to abut one third that of its initial response (FIG. 5). Both sensors 2 and 3, containing iodine produced stable $NH_3$ responses with lower hysteresis than sensor 1 and which remained virtually unchanged with time over a test period of 3 or 4 weeks. As can be seen in FIG. 6 (line 30), sensor 3 when exposed to 50 ppm $NH_3$ in air at a flow rate of 200 ml/min exhibited a very slow decline in response over a period of 10 weeks, in contrast to sensor 1 (line 31).

3. A sensor according to claim 2, wherein said iodine is bound to another compound to reduce its volatility.

4. A sensor according to claim 3, wherein said iodine is bound chemically to starch.

5. A sensor according to claim 1, wherein said sensor further comprises a permeation device containing an iodine source so as to provide a controlled release of iodine into the electrolyte.

6. A sensor according to claim 5, wherein said iodine source comprises solid iodine.

7. A sensor according to claim 1, wherein said diffusion barrier is at least one of a gas phase diffusion barrier and a Knudsen barrier.

8. A sensor according to claim 1, further comprising a reference electrode.

* * * * *